(12) United States Patent
Okamura

(10) Patent No.: US 10,018,588 B2
(45) Date of Patent: Jul. 10, 2018

(54) METHOD OF MEASURING PH OF ANALYTE SOLUTION, AND PH MEASURING DEVICE

(71) Applicant: KOCHI UNIVERSITY, Kochi-shi, Kochi (JP)

(72) Inventor: Kei Okamura, Kochi (JP)

(73) Assignee: KOCHI UNIVERSITY, Kochi-shi (JP)

( * ) Notice: Subject to any disclaimer, the term of this patent is extended or adjusted under 35 U.S.C. 154(b) by 0 days.

(21) Appl. No.: 15/511,793

(22) PCT Filed: Mar. 25, 2016

(86) PCT No.: PCT/JP2016/059632
§ 371 (c)(1),
(2) Date: Mar. 16, 2017

(87) PCT Pub. No.: WO2016/158755
PCT Pub. Date: Oct. 6, 2016

(65) Prior Publication Data
US 2017/0307563 A1    Oct. 26, 2017

(30) Foreign Application Priority Data

Mar. 30, 2015 (JP) ................................ 2015-069185

(51) Int. Cl.
*G01N 27/416*    (2006.01)
*G01N 27/36*    (2006.01)

(52) U.S. Cl.
CPC ......... *G01N 27/4167* (2013.01); *G01N 27/36* (2013.01)

(58) Field of Classification Search
CPC .......... G01N 27/4166; G01N 27/4167; G01N 27/36; G01N 27/28; G01N 27/4165; G01N 27/38; G01N 27/414
See application file for complete search history.

(56) References Cited

FOREIGN PATENT DOCUMENTS

| JP | 2001-242134 A | 9/2001 |
| JP | 2003-043007 A | 2/2003 |
| JP | 2010-107421 A | 5/2010 |
| JP | 2012-107986 A | 6/2012 |
| JP | 2012107986 A * | 6/2012 ............. G01N 27/48 |

OTHER PUBLICATIONS

Kimoto E et al, JP2012107986A, Jun. 2012, Machine Translation.*
Oct. 12, 2017 International Preliminary Report on Patentability issued in PCT/JP2016/059632.

(Continued)

*Primary Examiner* — Jermele M Hollington
*Assistant Examiner* — Suresh K Rajaputra
(74) *Attorney, Agent, or Firm* — Oliff PLC

(57) ABSTRACT

A simplified, rigorous and accurate method of measuring pH of an analyte solution with extreme precision, which does not cause errors against actual pH through compensating a pH variation by a liquid temperature or a concentration of potassium chloride of an internal liquid in a glass electrode or a reference electrode when pH is measured with respect to various analyte solutions such as a sample solution having a high concentration of salts, a sample solution contaminated with salts and a sample solution having a low concentration of salts.

10 Claims, 11 Drawing Sheets

(56) References Cited

OTHER PUBLICATIONS

Jun. 21, 2016 International Search Report issued in International Patent Application No. PCT/JP2016/059632.
"Handbook of methods for the analysis of the various patameters of the carbon dioxide system in sea water," DOE, version 2, A. G. Dickson & C. Goyet, eds. 1994.
Jan. 10, 2017 Office Action issued in Japanese Patent Application No. 2015-069185.

* cited by examiner

METHOD OF MEASURING PH OF ANALYTE SOLUTION, AND PH MEASURING DEVICE

TECHNICAL FIELD

The present invention relates to a method of measuring pH of various analyte solutions exemplified by a sample solution having high concentration of salts of marine water of the ocean and lake water of a brackish lake and so on and a plain water sample solution of rivers, lakes or marshes and so on to observe a global environment, and a sample solution contaminated with salts such as industrial undiluted drainage water and so on to protect an environment, and a pH measuring device therefor.

BACKGROUND OF THE ART

To observe change of a global environment, pH of sample solutions having high concentration of salts obtained from sea level or sea abyss in the ocean and plain water sample solutions obtained from rivers, lakes or marshes on land are measured. The measurement of pH is conducted on site or at a laboratory after obtaining thereof.

Recently, carbon dioxide included in the atmosphere has been gradually increased because of a large amount of artificial consumption of fossil fuels such as petroleum, coal and the like. Global warming has progressed. Carbon dioxide in the atmosphere has increased concentrations of hydrogen carbonate ions and carbonate ions by dissolving in marine water, land water, cloud and rainwater and thus, acidification of the ocean and so on has increased. By continuously and accurately measuring pH of marine water of the ocean, lake water of a brackish lakes and plain water of rivers, lakes or marshes and so on, change of the global environment is observed and a future environment on a global scale is forecasted. To take actions for preventing further environmental pollution and global warming, accurate pH data should be obtained.

An available and generalized pH meter is used so as to measure pH of ordinary analyte solutions such as tap water, dilute acid or alkaline test fluid and sample at room temperature maintained at a constant temperature of approximately 25° C. According to the pH meter, pH of the analyte solution can be measured from an electrochemical voltage between a glass electrode and a reference electrode. In this case, pH of the analyte solution is expressed as a hydrogen-ion exponent (pH=−log [$H^+$]; [$H^+$] represents a hydrogen-ion concentration in a solution). Actually, hydrogen-ion activity rather than the hydrogen-ion concentration itself is electrochemically measured. Because the hydrogen-ion activity approximately equals to the hydrogen-ion concentration in the ordinary analyte solution, pH thereof may be represented by the hydrogen-ion exponent.

It is difficult to accurately detect the hydrogen-ion concentration itself and the hydrogen-ion activity in the sample solution having high concentration of salts such as marine water, because of existence of co-existence ions with high concentration, interaction between the co-existence ions and the hydrogen ions, ion selectivity of electrodes, action of dissolved gases and the like. Therefore it is also difficult to rigorously measure pH of the sample solution having high concentration of salts.

Besides the hydrogen-ion exponent used in pH of the ordinary analyte solution, to represent pH of marine water, definitions of total scale pH (hereinafter referred to it as $pH_T$, $pH_T = -\log([H^+]+[HSO_4^-])$; [$H^+$] represents a hydrogen-ion concentration in the solution, and [$HSO_4^-$] represents a sulfate ion concentration therein.) and seawater scale pH (hereinafter referred to it as $pH_{sws}$, $pH_{sws}=-\log([H^+]+[HSO_4^-]+[F^-])$; [$H^+$] represents a hydrogen-ion concentration in the solution, [$HSO_4^-$] represents a sulfate ion concentration therein and [$F^-$] represents a fluorine ion concentration therein.) are disclosed by Non Patent Document 1. The total scale pH and the seawater scale pH are premised on measuring pH of marine water, and can be defined by conducting calibration of both of the glass electrode and the reference electrode. The calibration is conducted by using a calibration solution for measuring marine water (Tris-HCl buffer solution, AMP buffer solution and so on) which is prepared by dissolving a buffer into a solvent having composition similar to marine water or the same. Preparing of the calibration solution for measuring marine water requires complex steps and complicated works. In addition, the calibration solution for measuring marine water on site is not suitable for measuring pH of the analyte solution of collecting marine water of the ocean whose liquid temperature varies wide range from 0 to 35° C., because the pH thereof varies widely depending on a temperature just like one of the Tris-HCl buffer solution.

As a method for simply measuring pH of an analyte solution with extreme precision, Patent Document 1 discloses a method of measuring pH of a measurement solution as marine water by using a pair of electrodes consisting of a glass electrode and a reference electrode. A potential difference between the pair of the electrodes is regulated to 0 mV in a solution having range of pH 7.2 to 8.2. The pH of the measurement solution is measured according to a voltage generated between the electrodes.

According to the method, because the potential difference between the electrodes is needed to set to 0 mV, an internal liquid of the glass electrode have to be regulated to pH 7.2 to 8.2 by a concentration of saturated potassium chloride. When the measurement solution is marine water, the internal liquid employing a pH standard solution that approaches actual pH thereof is preferably used. According to a study by the present inventor, when potassium chloride was saturated in the pH standard solution, it has become clear that pH of the internal liquid was decreased by approximately 0.5 from original pH of the pH standard solution due to variation in an activity coefficient. A set condition in the method disclosed by Patent Document 1 therefore requires employing a pH standard solution having pH 7.7 to 8.7 as the internal liquid which meets a requirement of pH 7.2 to 8.2. As available pH standard solutions, JIS (Japanese Industrial Standard) buffer solutions includes a phthalate buffer solution of pH 4.01, a neutral phosphate buffer solution of pH 6.86, a phosphate buffer solution of pH 7.41 and a borate buffer solution of pH 9.17 at 25° C. as a constant temperature. But a pH standard solution which is stable in pH 7.7 to 8.7 is not available in a market. Further, unless original pH based on constituents of a pH buffer solution of internal liquids in the glass electrode and the reference electrode is carefully selected, errors thereof occur.

An aqueous solution consisting potassium chloride from 3.3 mol/L to saturation or an aqueous solution, in which potassium chloride and the JIS buffer solution that approaches pH of a sample solution such as marine water are co-existed, has been used for internal liquids of the glass electrode and the reference electrode. When measuring pH of an analyte solution such as marine water, pH thereof has been calculated from the voltage between the electrodes by using original pH of a pH standard solution as a basis without considering the concentration of potassium chloride and a liquid temperature in the internal liquid of the reference electrode.

When carbon dioxide included in the atmosphere dissolves in marine water, it generates hydrogen carbonate ions ($HCO_3^-$) and carbonate ions ($CO_3^{2-}$), and then these ions neutralize acid ($H^+$) and buffer it. Thereby pH of marine water approaches neutrality (approximately pH 7.4 to 8.2). To observe change of the global environment accurately, a variation of pH should be accurately and precisely detected down to 3 decimal places. A temperature of marine water in the ocean widely varies range from approximately 0 to 35° C. depending on a region and/or depth. However, the variation of pH, which is caused by the concentration of potassium chloride in the internal liquid and a liquid temperature thereof in the glass electrode and the reference electrode, has not been reflected. The errors between the actual pH and the above calculated pH therefore have occurred. Furthermore, the variation of pH has not able to be accurately and precisely detected down to 3 decimal at measurement places on site.

PRIOR ART DOCUMENT

Patent Document

[Patent Document 1] Japanese Patent Application Publication No.: JP2012-107986A1

Non-Patent Document

[Non-Patent Document 1] DOE (1994) Handbook of methods for the analysis of the various parameter of the carbon dioxide system in sea water. Version 2, A. G. Dickson & C. Goyet, eds. ORNL/CDIAC-74

SUMMARY OF THE INVENTION

Problems to be Solved by the Invention

The present invention was made in view of solving the above described problems, and its object is to provide a simplified, rigorous and accurate method of measuring pH of an analyte solution with extreme precision, which does not cause errors against actual pH through compensating a pH variation by a liquid temperature or a concentration of potassium chloride of an internal liquid in a glass electrode or a reference electrode when pH is measured with respect to various analyte solutions such as a sample solution having a high concentration of salts or a sample solution contaminated with salts as well as a sample solution having a low concentration of salts. And another object is to provide a simple pH measuring device which is used for the method.

Means for Solving Problems

A method of measuring pH of an analyte solution of the present invention developed to achieve the objects above described comprises:
using electrodes, in which a pair of the electrodes consists of a glass electrode which encloses a glass electrode internal liquid including potassium chloride and a glass electrode buffer solution inside and a reference electrode which encloses a reference electrode internal liquid including potassium chloride and a reference electrode buffer solution inside such that a potential difference between the pair of the electrodes is regulated to 0 mV in a solution having out-of-range of pH 7.2 to 8.2,
sensing a voltage generated between the electrodes in the analyte solution, and
detecting a pH value of the analyte solution while compensating pH by a concentration of the potassium chloride in the reference electrode internal liquid and a liquid temperature of the analyte solution.

It is preferable that the method of measuring pH of the analyte solution comprise further a step for converting the pH value of the analyte solution into a predetermined value thereof at room temperature.

It is preferable that the method of measuring pH of the analyte solution comprises:
a step for sensing the liquid temperature of the analyte solution,
a step for calculating a compensated pH value in the reference electrode internal liquid comprising:
    calculating a corrected pH value of the reference electrode buffer solution from an inherent pH value of the reference electrode buffer solution according to the liquid temperature,
    calculating a value of a potential variation of the reference electrode internal liquid according to the concentration of the potassium chloride thereof,
    calculating a deducted pH value of the reference electrode internal liquid from the value of the potential variation according to the liquid temperature, and then,
    compensating the deducted pH value of the reference electrode internal liquid from the corrected pH value of the reference electrode buffer solution,
a step for sensing the voltage generated between the electrodes in the analyte solution,
a step for detecting the pH value of the analyte solution comprising:
    calculating a pH difference from the voltage according to the liquid temperature, and then
    detecting the pH value of the analyte solution from the pH difference according to the compensated pH value of the reference electrode internal liquid.

The method of measuring pH of the analyte solution may comprise a step for converting the pH value of the analyte solution into a predetermined value thereof at room temperature.

In the method of measuring pH of the analyte solution, it is preferable that the glass electrode internal liquid and the reference electrode internal liquid are equivalent each other.

The glass electrode internal liquid and the reference electrode internal liquid may be saturated with the potassium chloride respectively, in the method of measuring pH of the analyte solution For the method of measuring pH of the analyte solution, it is preferable that the analyte solution is a salt-including sample solution or a plain water sample solution of selected from the group consisting of marine water, lake water and river water, or a sample solution contaminated with salts.

As regards the method of measuring pH of the analyte solution, the glass electrode has a glass sensing-membrane, and the reference electrode has a liquid junction.

In the method of measuring pH of the analyte solution, it is more preferable that a difference between the corrected pH value of the reference electrode internal liquid and the pH value of the analyte solution is 2 at maximum.

A pH measuring device for an analyte solution developed to achieve the another object above described comprises:

electrodes which consist of a glass electrode that encloses a glass electrode internal liquid including potassium chloride and a glass electrode buffer solution inside and a reference electrode that encloses a reference electrode internal liquid including potassium chloride and a reference electrode buffer solution inside such that a potential difference between the electrodes is regulated to 0 mV in a solution having out-of-range of pH 7.2 to 8.2, a voltage sensor which senses a voltage generated between the electrodes in the analyte solution where the electrodes are dipped therein, a temperature sensor which senses a liquid temperature of the analyte solution, calculating circuits which calculates a pH value of the analyte solution from the voltage while compensating pH by a concentration of the potassium chloride in the reference electrode internal liquid and the liquid temperature of the analyte solution.

Effects of the Invention

The method of measuring pH of the analyte solution of the present invention achieves to measure pH of the analyte solution such as a sample solution having a high concentration of salts, specifically marine water of sea level or sea abyss in the ocean, or lake water in a brackish lake with extreme precision and high repeatability, rigorously, accurately and simply. Furthermore, the method achieves to measure pH of other various analyte solution such as a plain water sample solution of rivers, lakes or marshes and so on and a sample solution contaminated with salts from plant facilities with extreme precision rigorously and accurately as well as the sample solution having the high concentration of salts.

According to the method of measuring pH of the analyte solution, a voltage generated between the electrodes of the glass electrode and the reference electrode is sensed, and the pH value of the analyte solution is detected from the voltage while compensating pH by a concentration of the potassium chloride in the reference electrode internal liquid and the liquid temperature of the analyte solution by using a mathematical conversion expression. Therefore, even if the liquid temperature of the analyte solution fluctuates on each measurement point or at each measurement time, pH of the internal liquids can be appropriately converted. In consequence, depending to compensating pH variation by the liquid temperature or the concentration of potassium chloride of the internal liquid in the glass electrode or the reference electrode, the accurate pH of the analyte solution can be measured without causing difference from actual pH.

By using the method of measuring pH of the analyte solution, pH can be accurately measured on any measurement points such as sea abyss in the ocean on site directly.

When using a pH standard solution of pH 7.41 saturated with potassium chloride as those internal liquids, the pH measuring device for the analyte solution of the present invention is used as a pH sensor on the ocean and so on where a potential becomes 0 mV at approximately pH 6.9. Also pH standard solutions of pH 4.01, pH 6.86 or pH 9.17 may be used according to pH of the analyte solution. The pH measuring device for the analyte solution has broad utility, because it may be used without changing features of commercially available glass electrodes or reference electrodes and with using commercially available pH standard solutions and potassium chloride.

The pH measuring device for the analyte solution of the present invention needs little electric requirements, and does not need specialty agents such as indicators for pH measurement. And since the pH measuring device has compact size and can be stably used in sea abyss such as 5000 m of water depth with little temperature drift, pH can be rigorously and accurately measured with extreme precision. Because pH is able to be stably measured without human assistance for long time continuously, the pH measuring device is able to measure pH at various water depth of the sea abyss or under change of pH according to elapsed time.

MODES FOR CARRYING OUT THE INVENTION

Hereunder, embodiments to practice the present invention in detail will be explained, but the scope of the present invention is not restricted by these embodiments.

Figure 1:
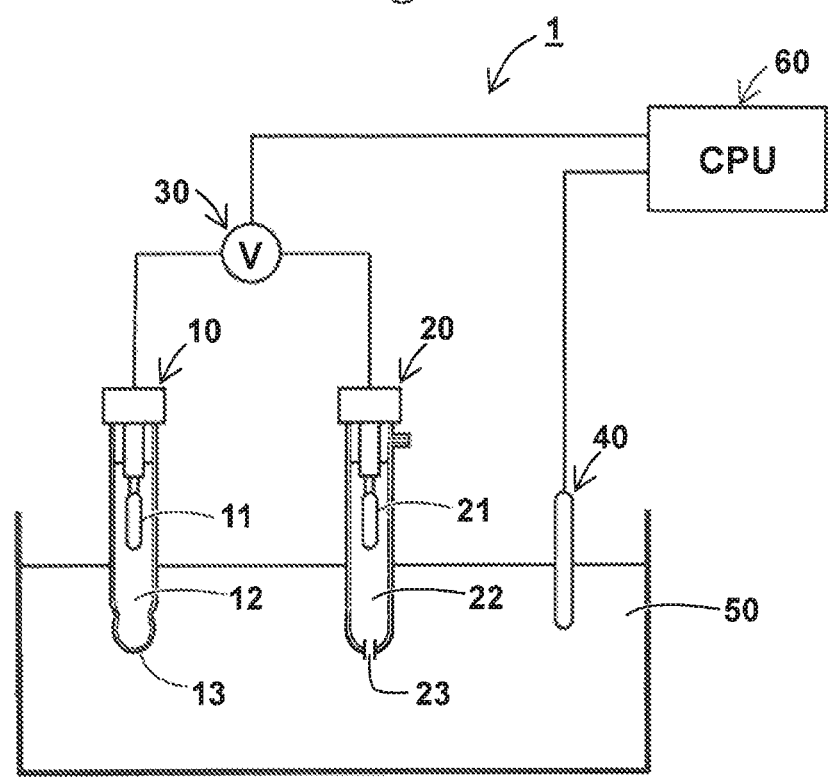
FIG. 1 is a schematic view showing a pH measuring device for used for a method of measuring pH of the analyte solution of the present invention.

A method of measuring pH of an analyte solution of the present invention is explained by an embodiment of marine water of the analyte solution, with referring FIG. 1.

The method of measuring pH of the analyte solution is carried out by using a pH measuring device 1 for the analyte solution, in which a voltage sensor 30 as a voltmeter and a temperature sensor 40 are respectively dipped at inferior sides thereof into the analyte solution 50 and are respectively connected at superior sides thereof to a central processing unit (CPU) 60 via connecting cords. The voltage sensor 30 is connected to a glass electrode 10 and a reference electrode 20, and senses a voltage (i.e. a potential difference). The CPU 60 has a sensing circuit which measures and senses a temperature on the temperature sensor 40, a calibration circuit which calibrates electrodes between the glass electrode 10 and the reference electrode 20 and a memory circuit thereof, a sensing circuit which measures and senses the voltage between the glass electrode 10 and the reference electrode 20, an arithmetic circuit which compensates a pH variation by a liquid temperature and a concentration of potassium chloride of internal liquids in the glass electrode and the reference electrode and detects actual pH of the analyte solution, an arithmetic circuit which converts the pH value of the analyte solution into predetermined value thereof at room temperature, and a memory circuit which stores the pH results obtained.

As regards the glass electrode 10, an inferior top of a glass tube is sealed with a thin pH sensing glass, a glass electrode internal liquid 12 is filled up therein, and an internal electrode 11 of an Ag/AgCl electrode is soaked there. As regards the reference electrode 20, an inferior top of a glass tube is sealed and provided with a liquid junction 23 such as microporous or porous ceramics and a fitting-glass sleeve, a reference electrode internal liquid 22 is filled up therein, and an internal electrode 21 of an Ag/AgCl electrode is soaked there. It has been known that pH of marine water is approximately pH 7.4 to 8.2. Therefore, the internal liquids, in which potassium chloride is saturated in a phosphate buffer solution of pH 7.41 (JIS: Japanese Industrial Standards) that approaches pH of marine water, is used for the glass electrode internal liquid 12 and the reference electrode internal liquid 22.

Since various salts are dissolved in the marine water, it is decided to measure $pH_T$ (i.e. total scale) which is widely used for indicating pH of the marine water.

When it is indicated by:

$$pH_F = [H^+]_F$$

(in the equation, $pH_F$ is free scale pH, $[H^+]_F$ is a concentration of free hydrogen ions), it is shown as:

$$[H^+]_T = [H^+]_F (1 + S_T/K_S) \approx [H^+]_F + [HSO_4^-] \quad (1)$$

(in the equation (1), $S_T = [HSO_4^-] + [SO_4^{2-}]$, and $K_S = [H^+]_F [SO_4^{2-}]/[HSO_4^-]$), and $$pH_T = -\log([H^+]_T/(\text{molkg-soln}^{-1})) \quad (2).$$

Therefore, $pH_T$ is defined by the equations (1) and (2).

Figure 2:
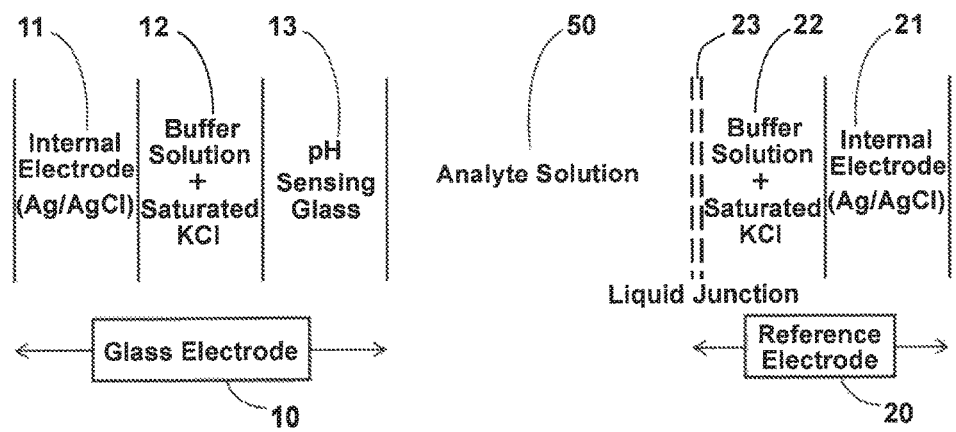
FIG. 2 is a schematic view of a principle showing relationship between a glass electrode and a reference electrode used for a method of measuring pH of an analyte solution of the present invention.

When pH is measured while referring FIG. 2 which indicates a principle of pH measurement between the glass electrode 10 and the reference electrode 20, Nernst's equation:

$$E_e = E° + (RT/nF)\log a_O/a_R \quad (3)$$

(in the equation, $E_e$ is an electrode potential under an equilibrium condition between Ox+ne and Red of an electrode reaction [Ox is a compound having a oxidative state, and Red is a compound having reductive state], $a_O$ and $a_R$ are respectively activity factors under Ox and Red conditions, E° is $E_e$ value when $a_O = a_R = 1$, R is a gas constant, T is temperature (K), and F is Faraday constant) is established.

When pH values of the internal liquid 12 (i.e. the buffer solution and the saturated KCl solution) in the glass electrode 10 are changed, equipotential pH may be changed thereby. If no potential difference between Ag/AgCl electrodes 11 and 21 of a side of the glass electrode 10 and a side of the reference electrode 20 is found and the potential of the liquid junction 23 is negligibly small, the equipotential pH can be pH of the internal liquid 12 in the glass electrode 10. In other words, when equivalent analyte solutions having the same pH are measured with using equivalent internal liquids of the internal liquid 12 (i.e. the buffer solution and the saturated KCl solution) in the glass electrode 10 and another internal liquid 22 (i.e. the buffer solution and the saturated KCl solution) in the reference electrode 20, it means that solutions having the same compositions with boundary as the pH sensing glass 13 will be measured. In the occasion, no potential is occurred between the glass electrode 10 and the reference electrode 20, therefore the equipotential pH indicates 0 mV of the pair of the electrodes.

Figure 3:
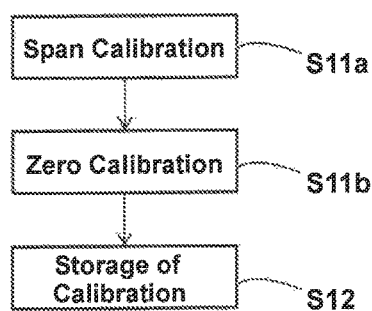
FIG. 3 is a process drawing for calibration of a method of measuring pH of an analyte solution of the present invention.

Then, calibration of the electrodes is carried out as shown in FIG. 3. When the analyte solution is the marine water, the calibration of the electrodes is carried out by using calibration solutions (Tris buffer solution, AMP buffer solution and so on) which are prepared as standard solutions by dissolving a buffer solution into a solvent whose composition is close to one of marine water.

Since internal liquids are respectively equivalent so that the glass electrode 10 and the reference electrode 20 indicate 0 mV of the pair of the electrode to become the equipotential pH as shown in FIG. 2, thus calibration can essentially be doubled as zero calibration. However, an asymmetric potential is practically generated due to the liquid junction 23. Accordingly span calibration is conducted by using two calibration solutions whose pH is different each other, first of all (S11a Step). And then, zero calibration is conducted so as to coincide with pH value of one of the calibration solutions (S11b Step). The results of the calibration are stored into CPU 60 (S12 Step).

Figure 4:
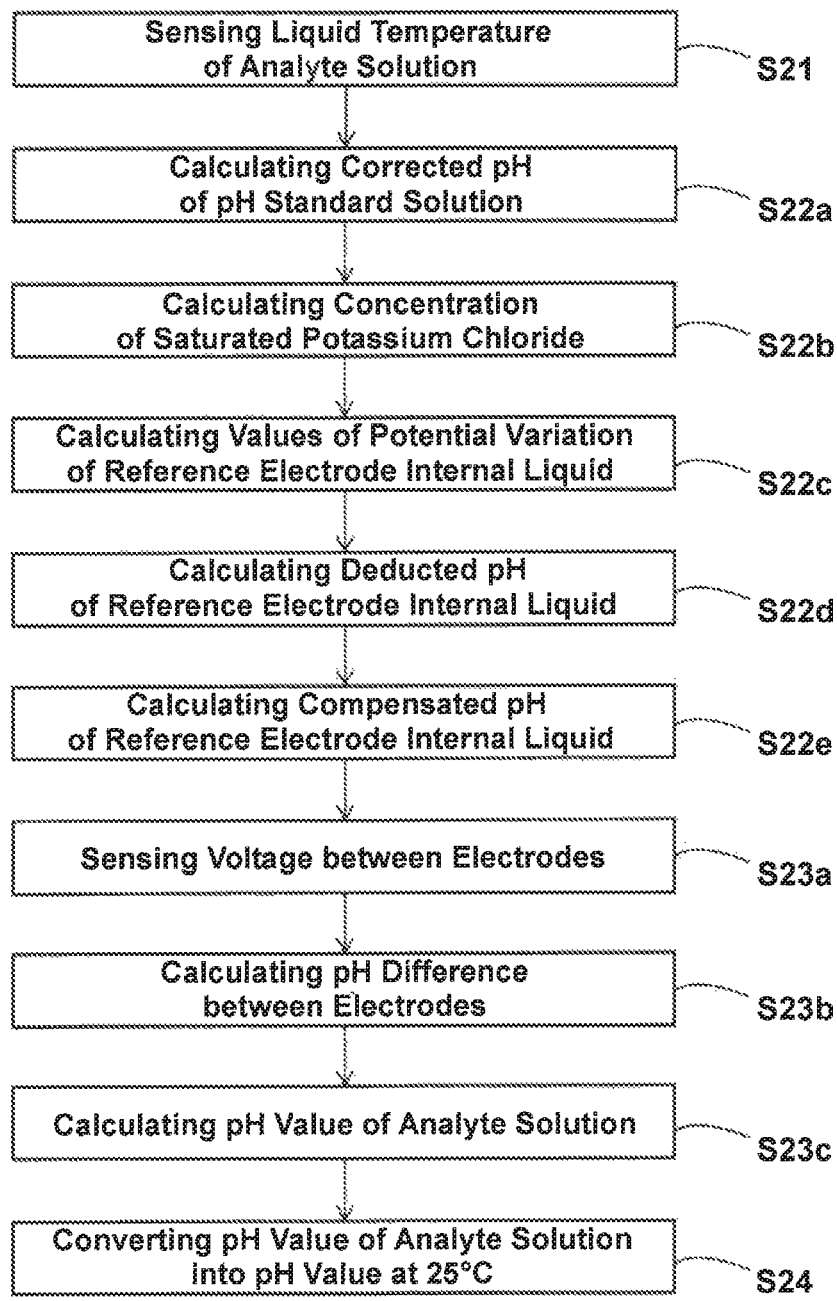
FIG. 4 is a process drawing for pH measurement of a method of measuring pH of an analyte solution of the present invention.

Next, pH measurement of the analyte solution 50 is carried out according to FIG. 4.

At the beginning, the liquid temperature of the analyte solution 50 is sensed with a temperature sensor 40 such as a thermistor and a thermocouple as below (S21 Step). The liquid temperature is measured and sensed by the sensing circuit which senses it from a resistance value of the thermistor or an electromotive force of the thermocouple, which correspond to a temperature. The liquid temperature of the analyte solution 50 corresponds to liquid temperatures of the glass electrode internal liquid 12 and the reference electrode internal liquid 22.

Figure 5:
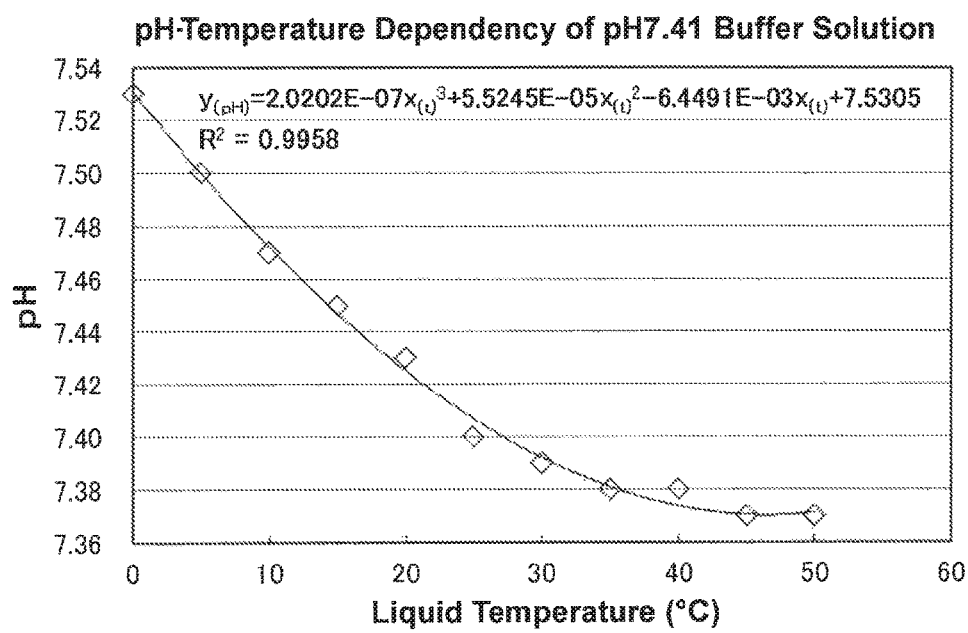
FIG. 5 is a graph showing a correlation between pH and a liquid temperature of a pH standard solution of pH 7.41 which are used for a method of measuring pH of an analyte solution of the present invention.

And then, pH of the reference electrode internal liquid 22 of the saturated potassium chloride buffer solution is compensated as below (S22 Step).

pH depends on the liquid temperature, as shown in FIG. 5 which indicates a correlation between pH and a liquid temperature of a pH standard solution as regards to the pH standard solution which has a composition of the reference electrode internal liquid 22 and has inherent value of pH 7.41 at 25° C. Therefore, pH of the pH standard solution as the reference electrode buffer solution is corrected according to the liquid temperature while referring FIG. 5 (S22a Step). For example, the corrected pH value of the reference electrode buffer solution is calculated according to the liquid temperature in accordance with an approximate expression (concretely, $y_{(pH)}=2.0202\times10^{-7}\times x_{(t)}^3+5.5245\times10^{-5}\times x_{(t)}^2+6.4491\times10^{-3}\times x_{(t)}+7.5305$; $y_{(pH)}$ is the corrected pH value, $x_{(t)}$ is the liquid temperature, a coefficient of the correlation: $R^2=0.9958$), as shown in FIG. 5 which indicates temperature dependency of the pH standard buffer solution of pH 7.41. Incidentally, after preparing a preliminary table of pH of the pH standard solution according to the liquid temperature thereof, the corrected pH values may be read from the table according to the liquid temperature.

Figure 6:
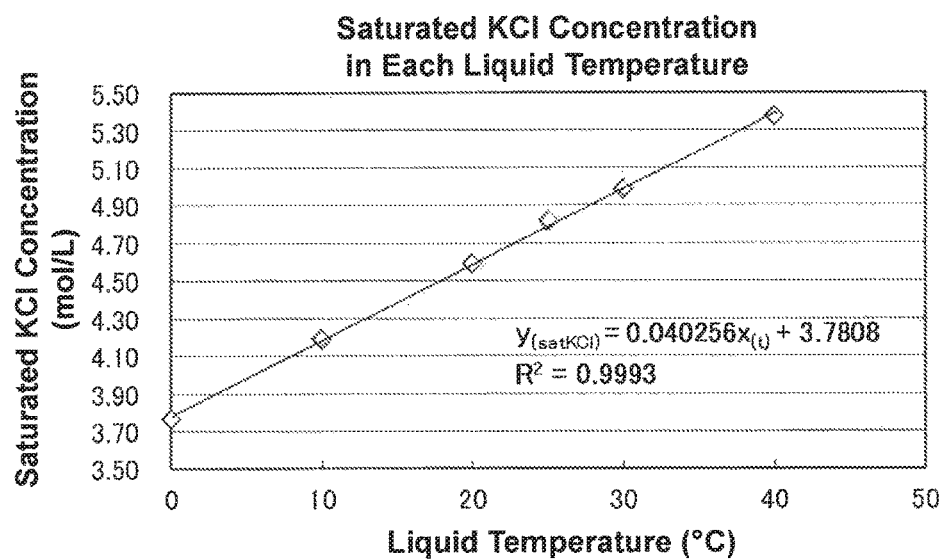
FIG. 6 is a graph showing a correlation between a concentration of saturated potassium chloride and a liquid temperature thereof, which is used for a method of measuring pH of an analyte solution of the present invention.

As shown in FIG. 6 which indicates a correlation between the concentration of saturated potassium chloride and the liquid temperature thereof, the concentration thereof depends on the liquid temperature thereof. Therefore the concentration of saturated potassium chloride in the reference electrode internal liquid 22 is calculated according to the liquid temperature in accordance with FIG. 6. For example, as shown in FIG. 6, the concentration of the saturated potassium chloride is calculated according to the liquid temperature in accordance with an approximate expression (concretely, $y_{(satKCl)}=0.040256\times x_{(t)}+3.7808$; $y_{(satKCl)}$ is the concentration of the saturated potassium chloride, $x_{(t)}$ is the liquid temperature, a coefficient of the correlation: $R^2=0.9993$) (S22b Step). Incidentally, after preparing a preliminary table of the concentration of the saturated potassium chloride according to the temperature thereof, the concentration of saturated potassium chloride may be read from the table according to the liquid temperature.

Figure 7:
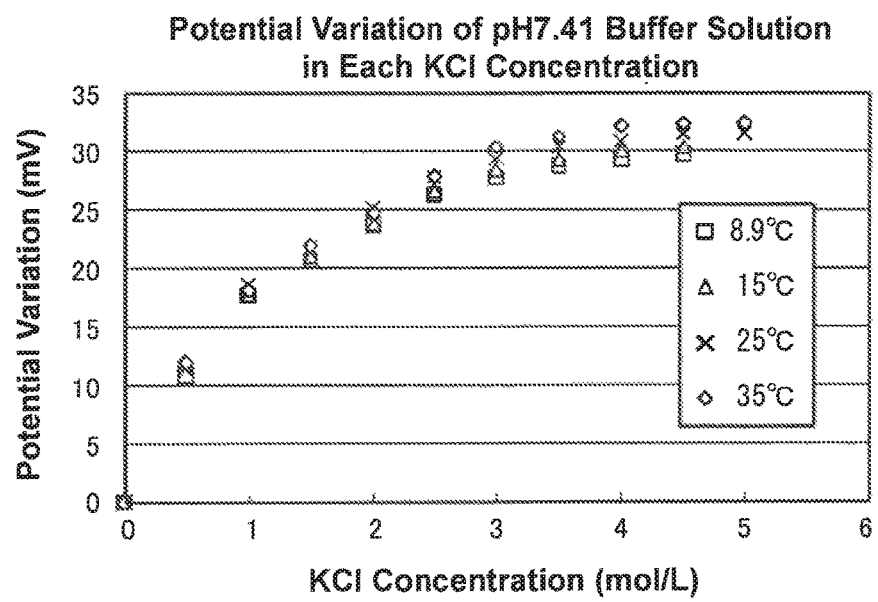
FIG. 7 is a graph showing a correlation between a potential variation and a concentration of potassium chloride which is used for a method of measuring pH of an analyte solution of the present invention.

As shown in FIG. 7 which indicates a correlation with respect to each temperature between a potential variation and a concentration of potassium chloride which co-exists with a pH standard solution of pH 7.41 (25° C.), the potential variation depends on the concentration of potassium chloride and the temperature. When the above-mentioned Nernst's equation of the equation (3) is modified, the Nernst response is recognized. As regards Nernst response, the potential variation is proportional to absolute temperature according to electrochemical requests and $$\text{every pH 1 at 25° C., 0.059160V} \quad (4)$$

$$\text{every pH 1 at } t \text{ ° C., } 0.059160\text{V}\times(273.15+t \text{ ° C.})/(273.15+25.00\text{° C.}) \quad (5).$$

Figure 8:
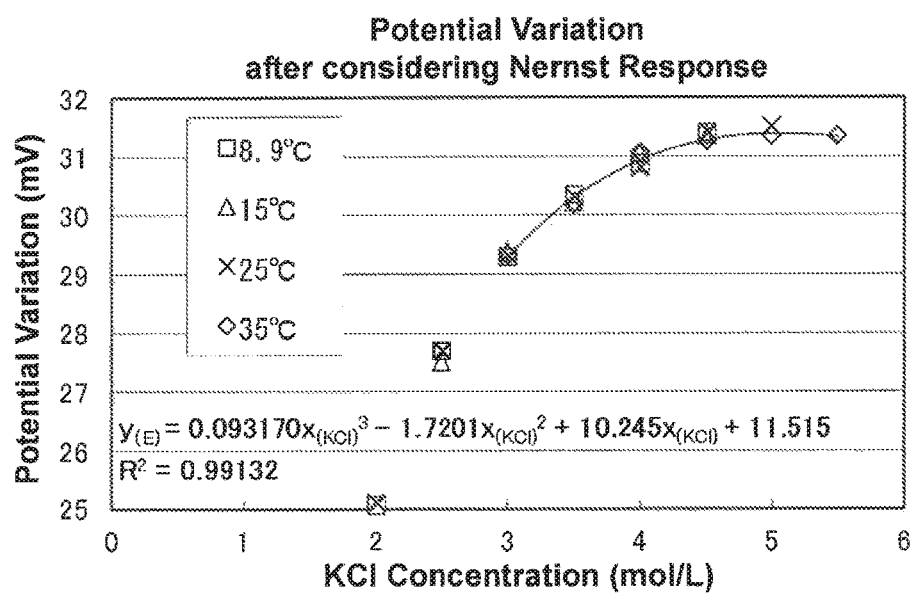
FIG. 8 is a graph showing a correlation between a concentration of potassium chloride and a potential variation under considering Nernst response, which is used for a method of measuring pH of an analyte solution of the present invention.

As considering thus Nernst response based on FIG. 7, plots of every temperature are almost overlapped, and values of the potential variation consolidated at 25° C. correlates with the concentration of potassium chloride (see the plots at 25° C.) as shown in FIG. 8. Therefore, the values of the potential variation of the reference electrode internal liquid 22 at 25° C. are calculated according to the concentration of potassium chloride in accordance with FIG. 8 (S22c Step). For example, the values of the potential variation of the reference electrode internal liquid 22 are calculated as conversion at 25° C. according to an approximate expression (concretely, $y_{(E)}=0.093170\times x_{(KCl)}^3+1.7201\times x_{(KCl)}^2+10.245\times x_{(KCl)}+11.515$, within ranging from 3.0 to 5.5 mol/L; $y_{(E)}$ is the values of the potential variation, $x_{(KCl)}$ is the concentration of potassium chloride, a coefficient of the correlation: $R^2=0.9913$). Incidentally, after preparing a preliminary table of values of the potential variation according to the concentration of potassium chloride, the values of the potential variation may be read from the table according to the concentration of the potassium chloride.

Values of deducted pH of the reference electrode internal liquid 22 are calculated from the calculated value of the potential variation according to the liquid temperature of the analyte solution 50 in accordance with the Nernst response of the equation (5) (S22d Step). Concretely the values of the potential variation calculated from the concentration of the saturated potassium chloride at room temperature (ca. 25° C.) are raised to 30 mV approximately. Since the values of the deducted pH are 0.5 approximately, decrease of pH of the reference electrode internal liquid 22 in thus case corresponds to approximately 0.5.

Then, the compensated pH value of the reference electrode internal liquid 22 is calculated from the corrected pH value of the reference electrode buffer solution by compensating the deducted pH of the reference electrode internal liquid 22 (S22e Step). Concretely, the deducted pH value (ca. 0.5), which corresponds to the value of the potential variation (ca. 30 mV) calculated from the concentration of the saturated potassium chloride at room temperature (ca. 25° C.), is subtracted from the corrected pH value of the reference electrode buffer solution, thereupon the compensated pH value of the reference electrode internal liquid 22 can be calculated.

Finally, a pH value of the analyte solution 50 is detected as below (S23 Step).

A voltage, which is generated between the electrodes of the glass electrode 10 and the reference electrode 20 in the analyte solution 50, is sensed by a voltage sensor (S23a Step). The voltage as a voltage value is input into CPU 60.

A pH difference, which is sensed between the electrodes of the glass electrode 10 and the reference electrode 20, is calculated from the voltage value in accordance with Nernst response of the equation (5) according to the liquid temperature of the analyte solution 50 (S23b Step).

pH values of the analyte solution 50 are calculated from the calculated pH difference according to the corrected pH values of the reference electrode internal liquid 22 (S23c Step), thereupon pH of the analyte solution 50 can be detected.

If necessary, the obtained pH values of the analyte solution 50 according to the liquid temperature may be converted into pH values at 25° C. according to the Nernst response of the equation (5) or a theoretical equation of a carbon dioxide equilibrium described in non-patent document 1 (S24 Step).

In this occasion, pH of marine water, which are detected as pH of the analyte solution 50 from each electrode potential of the glass electrode 10 and the reference electrode 20, are succinctly represented as follows.

As regards the glass electrode 10, a potential between the marine water 50 and the glass electrode internal liquid 12, which is proportional to difference of concentrations of hydrogen ions therebetween, is generated on a pH sensing glass 13. And a potential, which is proportional to a concentration of chlorine, is generated on an internal electrode 11 of Ag/AgCl. When pH of the marine water is represented by marine water pH and pH of the glass electrode internal liquid 12 is represented by internal liquid (g) pH, the following relational expressions are established between a marine water potential of the marine water 50, an internal liquid potential g of the glass electrode 10 and an electrode potential g of the glass electrode 10 at 25° C.:

internal liquid potential $g$=marine water potential+ (marine water pH−internal liquid $(g)$pH)× 0.059160    (6)

electrode potential $g = f_{(KCl\ concentration\ g)}$+internal liquid potential $g$    (7)

electrode potential $g = f_{(KCl\ concentration\ g)}$+marine water potential+(marine water pH−internal liquid$(g)$pH)×0.059160    (8)

(in the expressions, $f_{(KCl\ concentration\ g)}$ is a potential correction term attributed by the concentration of potassium chloride in the glass electrode internal liquid).

On the other hand, as regards the reference electrode 20, potentials between the marine water 50 and the reference electrode internal liquid 22 are commensurate by the liquid junction 23. And the potential, which is proportional to the concentration of chlorine, is generated on the internal electrode 21 of Ag/AgCl.

The following relational expressions are established between the marine water potential of the marine water 50, an internal liquid potential r of the reference electrode and an electrode potential r of the reference electrode 20:

internal liquid potential $r$=marine water potential    (9)

electrode potential $r = f_{(KCl\ concentration\ r)}$+internal liquid potential $r$    (10)

electrode potential $r = f_{(KCl\ concentration\ r)}$+marine water potential    (11)

(in the expressions, $f_{(KCl\ concentration\ r)}$ is a potential correction term attributed by the concentration of potassium chloride in the reference electrode internal liquid).

Since the glass electrode internal liquid 12 of the glass electrode 10 and the reference electrode internal liquid 22 of the reference electrode 20 are the saturated potassium chloride solutions using the same buffer solutions, the concentrations thereof are commensurate each other. The concentrations of potassium chloride in the internal liquids 12 and 22 of the glass electrode 10 and the reference electrode 20 hold KCl concentration g=KCl concentration r. Since $f_{(KCl\ concentration\ g)} = f_{(KCl\ concentration\ r)}$ and internal liquid (g) pH=internal liquid (r) pH, a potential (i.e. a potential difference) between the electrodes at 25° C. is obtained by representing buffer solution pH from the equations (8) and (11) as the following equation:

(electrode potential $g$−electrode potential $r$)(V)=(marine water pH−buffer solution pH)×0.059160(V)    (12).

The internal liquid (g) pH and the internal liquid (r) pH depend on the liquid temperature of the marine water 50 and the concentration of potassium chloride depends thereon. Therefore necessary information for measuring pH of the marine water are ultimately a voltage generated between the electrodes of the glass electrode 10 and the reference electrode 20, and the liquid temperature for leading pH of reference electrode internal liquid in the reference electrode 20. pH of the marine water, which is converted into one of predetermined temperature such as 25° C., is precisely obtained according to Nernst response of the equations (5) and (12) from thus information. More concretely, pH at 25° C. are calculated by using a theoretical equation of a carbon dioxide equilibrium.

As mentioned above, according to the method of measuring pH of the analyte solution of the present invention, accurate pH of the analyte solution 50 can be strictly measured by the liquid temperature of the analyte solution 50 and the voltage between the electrodes of the glass electrode 10 and the reference electrode 20, when commensurate buffer solutions saturated with potassium chloride are used for the internal liquid 12 of the glass electrode 10 and the internal liquid 22 of the reference electrode 20.

As regards a glass electrode used for a prior method of measuring pH, an internal liquid has been used for measuring pH as premises at approximate room temperature (ex. 25° C.). For the internal liquid, a buffer solution of approximate pH 7 having a concentration of 3.3 mol/L of potassium chloride solution, in which potassium chloride does not deposited even at 0° C., has been used. Or for an internal liquid is used for measuring pH as premises for sea abyss, a solution of 3.3 mol/L of a potassium chloride solution including 0.1 to 0.0001 mol/L of hydrochloric acid (which corresponds to pH 1 to 4).

In the cases of the prior methods, an exact concentration of potassium chloride is not guaranteed. And the internal liquid of the reference electrode is the saturated potassium chloride solution. Therefore, in concentrations of potassium chloride of the internal liquids 12 and 22 in a glass electrode and a reference electrode, KCl concentration g is not equal to KCl concentration r, and $f_{(KCl\ concentration\ g)}$ is not equal to $f_{(KCl\ concentration\ r)}$ thereby. In consequence, a potential correction term attributed by the concentration of potassium chloride in the reference electrode internal liquid is remained, therefore it is necessary to correct it.

And 2-point calibration is usually performed by using pH standard solutions according to pH of the analyte solution. For example, if pH of the analyte solution is approximately pH 7, pH standard solutions of pH 6.86 and 4.01, or other pH standard solutions of pH 6.86 and 9.17 are used for the calibration. However, every manufactures thereof will adopt to compensate or adjust dependency of pH in the pH standard solutions for such reference electrode internal liquid according to the concentration of included potassium chloride thereof in accordance with fairly different ways under their experiments.

And when 3.3 mol/L of a potassium chloride solution including 0.1 to 0.0001 mol/L of hydrochloric acid is used for the glass electrode internal liquid, it is estimated that the internal concentration or internal pH thereof is constant anytime. However, if the hydrochloric acid in the internal liquid includes 0.0001 mol (pH 4), the potential difference of marine water of pH 7.4 as the analyte solution is (7.4−4.0)×0.0591=0.201V=201 mV and the potential difference of marine water of pH 8.2 as the analyte solution is (8.2−4)×0.059=0.248V=248 mV. Therefore, it is necessary to sense the potential difference of approximately 200 to 250 mV strictly.

The above-mentioned embodiments of the present invention is enable to advantageously overcome thus problems of the prior art, because the predetermined pH buffer solution saturated with potassium chloride as the glass electrode internal liquid 12 or the reference electrode internal liquid 22.

The embodiments are mentioned, in which the analyte solution is the marine water and the internal liquid of the phosphate buffer solution of pH 7.41 saturated with potassium chloride at 25° C. is used for the glass electrode internal liquid 12 and the reference electrode internal liquid 22. However, pH of analyte solutions having comparable pH with marine water may be similarly measured. When pH of the analyte solutions except for the marine water are measured, it is possible that pH is preliminarily measured, and then the internal liquid of a phthalate buffer solution of pH 4.01, a neutral phosphate buffer solution of pH 6.86 or a borate buffer solution of pH 9.17 at 25° C., all of which are saturated with potassium chloride, may be used according to preliminarily measured pH. In those cases, pH is similarly measured except for calculating the potential variation using an approximate expression after consideration of Nernst corresponding to FIG. 8, a calibration curve or a correspondence table being comparable therewith according to the concentration of potassium chloride.

A pH buffer solution with unsaturated potassium chloride may be used as the glass electrode internal liquid 12 or the reference electrode internal liquid 22 instead of the internal liquid saturated with potassium chloride. However, in this case, pH is similarly measured except for calculating the potential variation according to FIG. 7.

A pH measuring device may continuously or intermittently measure pH, and may have a memory device for recording pH data and so on in CPU 60. Further, the pH measuring device may have a transmission device which transmits pH data and so on to a shipboard facility or management facilities through wired or wireless communication. The pH measuring device may be provided with a water sampler device which can continuously or intermittently perform measuring pH of the analyte solutions and sampling them in the occasion to bring back them.

Although it is mentioned that the glass electrode, the reference electrode and the temperature sensor are independent as the embodiments, they may be unified as so-called composite electrode.

DESCRIPTION OF EMBODIMENTS

Example of immediately measuring pH of marine water on site in abyss sea according to a method of measuring pH of an analyte solution of the present invention and Reference Example of immediately measuring pH of marine water on site in abyss sea according to a prior method of measuring pH which does not apply the present invention will be described below.

EXAMPLE 1

Figure 9:
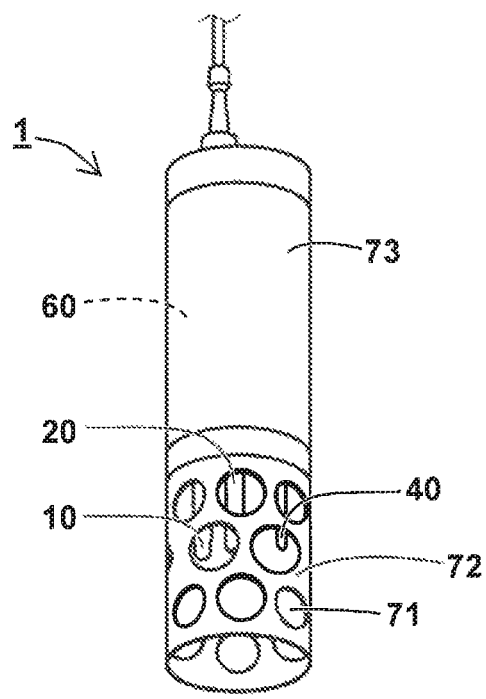
FIG. 9 is a schematic perspective outline view showing appearance of a pH measuring device for an analyte solution of the present invention.

A method of measuring pH of an analyte solution of the present invention was performed by using a pH measuring device 1 as shown in FIG. 1. pH electrodes of a glass electrode 10 and a reference electrode 20 were calibrated by 2-point calibration using Tris buffer solution and AMP buffer solution (see FIG. 3). A pH sensing glass 13 of the glass electrode 10 and a liquid junction 23 of the reference electrode 20 were exposed at the tops thereof. The electrodes were accommodated in an opened cylindrical cover 72 having many passing water holes 71, as shown in FIG. 9. CPU 60 was accommodated in a pressure resistance vessel 73. An internal liquid 12 in a pH sensor for marine water: PH12, which is available from KIMOTO ELECTRIC CO., LTD. as the glass electrode 10 and is a trade name, and an internal liquid 22 in a reference electrode 20 were used for internal liquids of a phosphate buffer solution of pH 7.41 at 25° C. (Japanese Industrial Standards) saturated with potassium chloride.

In an ocean area under where there are offshore submarine volcanos located at 350 m of a water depth in the Pacific Ocean, the hanged pH measuring device 1 from a ship was immersed under a rate of about 0.5 m/s from a sea level to 340 m of the water depth where are above the submarine volcanos, and then was hoisted up under a rate of about 0.5 m/s to the sea level. In the circumstance, pH data were obtained after measuring pH every second. Coinstantaneously, liquid temperatures of the marine water were measured by a temperature sensor 40. Besides, the marine water as analyte solutions were sampled at every 50 m up to 300 m of the water depth and every 20 m after 300 m thereof.

Figure 10:
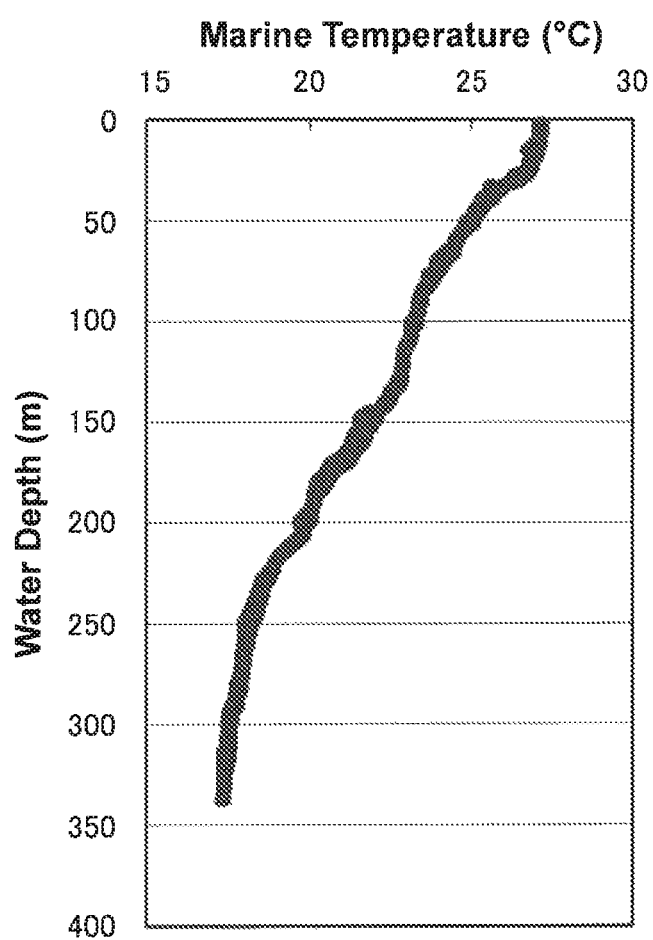
FIG. 10 is a graph showing a correlation between a water depth on a measurement marine area and a temperature of marine water as a liquid temperature of an analyte solution when a method of measuring pH of an analyte solution of the present invention is used.
Figure 11:
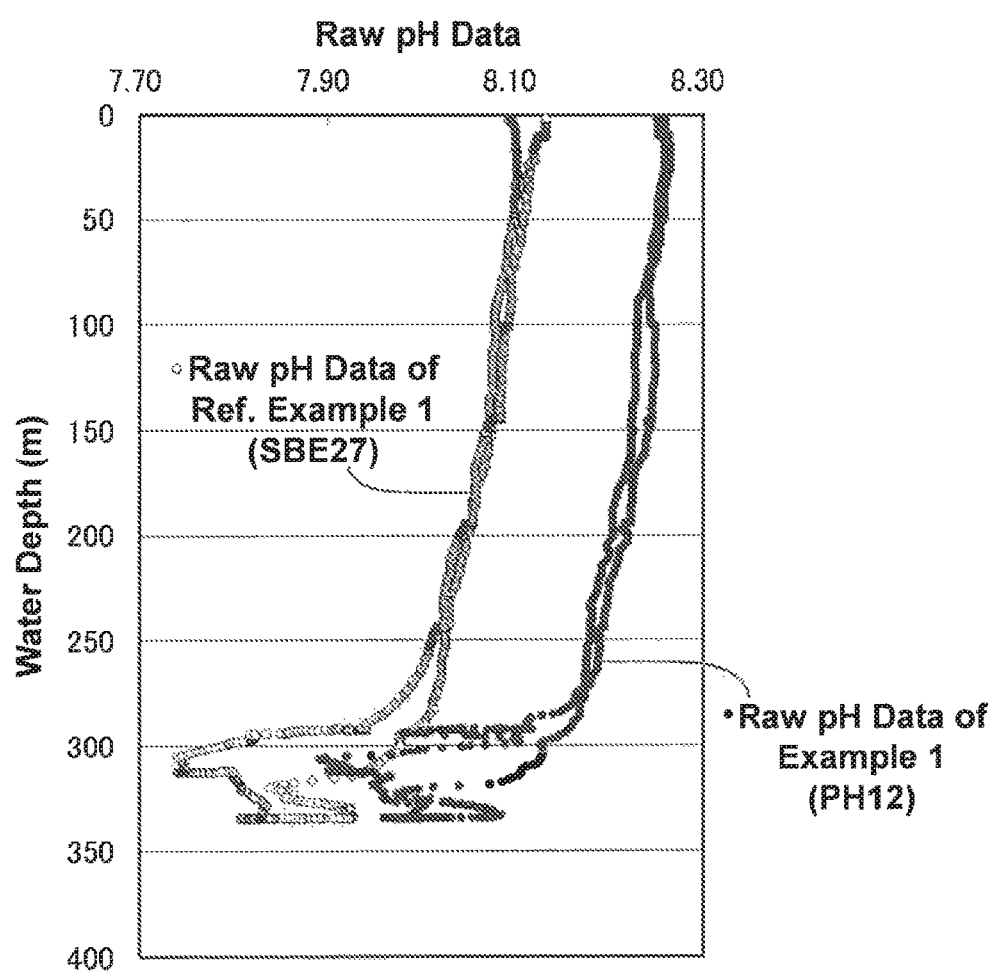
FIG. 11 is a graph showing a correlation between raw pH data of results of pH measurement according to Example 1 which is applied with a method of measuring pH of an analyte solution of the present invention and raw pH data of results of pH measurement according to Reference Example 1 which is not applied with the present invention, and a water depth.
Figure 12:
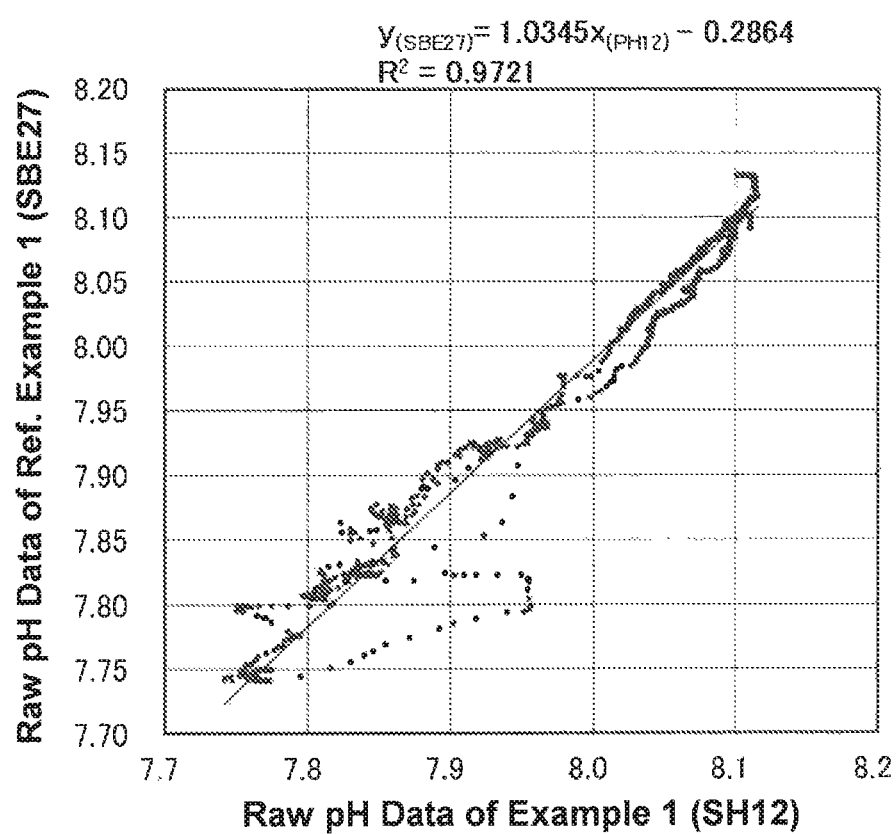
FIG. 12 is a graph showing a correlative relationship between raw pH data of results of pH measurement according to Example 1 which is applied with a method of measuring pH of an analyte solution of the present invention and raw pH data of results of pH measurement according to Reference Example 1.

Reference Example 1 pH was coinstantaneously measured by using pH sensor: SBE27 having a glass electrode and a reference electrode which is available from Sea-bird corporation and is a tradename, with using pH sensor for marine water: PH12.
(Contradistinction of Measured pH Data)
(1) Measuring Marine Water Temperature FIG. 10 illustrates a correlation between a water depth on the measurement marine area and temperatures of the marine water as the liquid temperature of the analyte solution. The liquid temperature corresponds to temperatures of the internal liquids 12 and 22 of the glass electrode 10 and the reference electrode 20.
(2) Raw Data of Measured pH FIG. 11 illustrates a correlation between raw pH data of results of pH measurement (see S22 to S23 in FIG. 4) according to Example 1 and raw pH data of results of pH measurement according to Reference Example 1. As shown in FIG. 11, shapes of vertical profile data in both results are almost same, although absolute values thereof are different. The reasons are that calibrations of both sensors were not concurrently preformed and that the used calibration solutions were different and difference of passage time after calibration was occurred.
(3) Correlation Between Raw Data of Measured pH FIG. 12 illustrates a correlative relationship between the raw pH data of the results of pH measurement according to Example 1 and the raw pH data of the results of pH measurement according to Reference Example 1. Although a little correlation thereof is diverged due to portions of variable pH change over 260 m or more of water depth, a highly-proportional correlative relationship is holistically recognized due to a coefficient of the correlation: $R^2=0.9721$, as shown in FIG. 12.
(4) Various pH Expressions of Results of pH Measurement in Example 1

Figure 13:
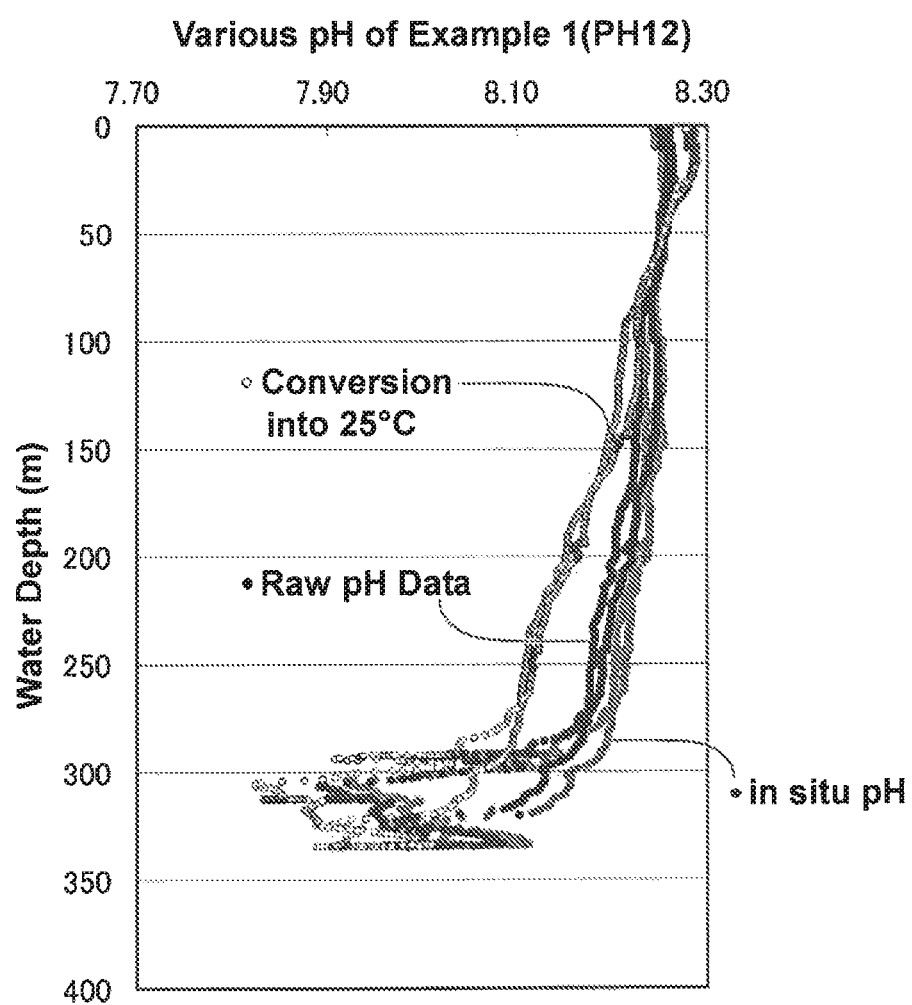
FIG. 13 is a graph showing a correlation between raw pH data of results of pH measurement according to Example 1 which is applied with a method of measuring pH of an analyte solution of the present invention, pH (in situ pH) at a temperature of marine water in a measurement area on site and pH which was converted into one of 25° C., and a water depth.

FIG. 13 illustrates the raw pH data of the results of pH measurement according to Example 1 (which was a compensated pH after putting off the temperature dependency of the electrodes), and converted pH data at 25° C. which was calculated by using a theoretical equation of a carbon dioxide equilibrium therefrom (see S24 in FIG. 4). Incidentally, in situ pH (i.e. pH at temperature of the marine water for measurement on site) are also illustrated.
(5) Reasonability of Converted pH Values at 25° C.

Figure 14:
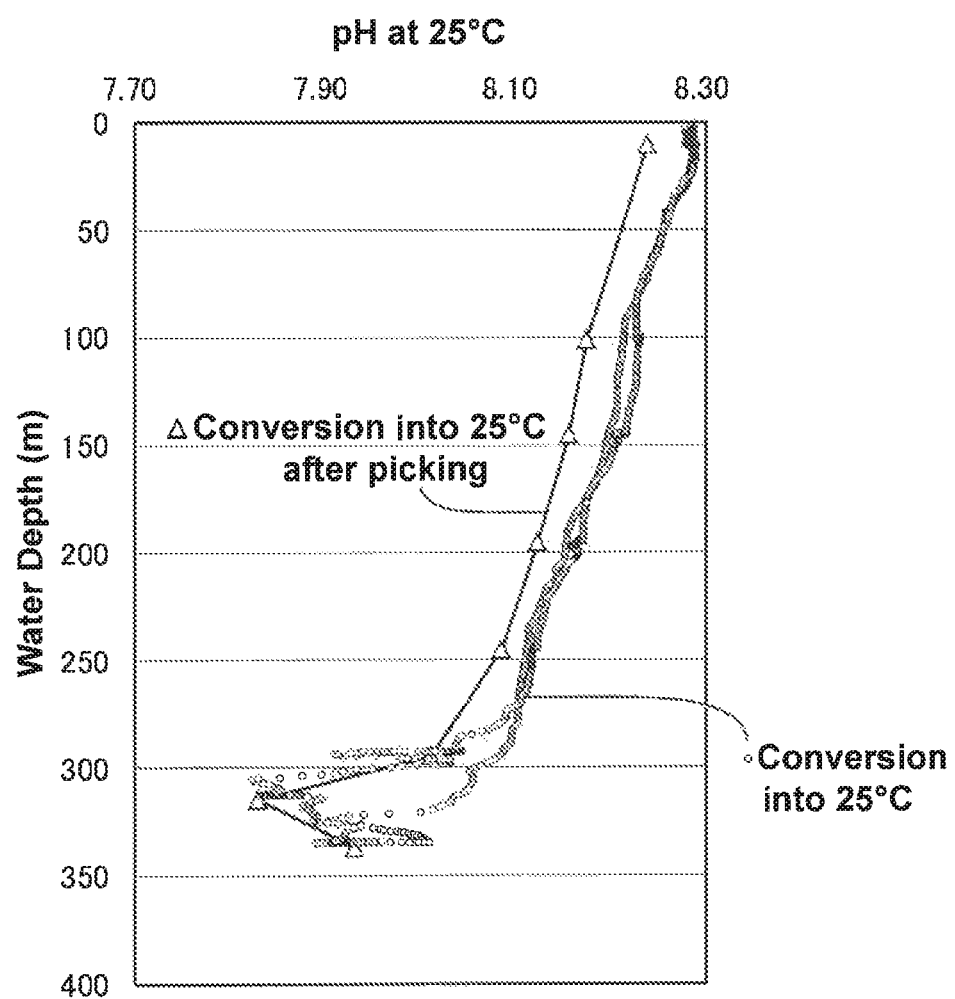
FIG. 14 is a graph showing a correlation between pH data of pH measurement according to Example 1 which are converted from results thereof into one of 25° C. and are applied with a method of measuring pH of an analyte solution the present invention, and actual pH data which are afterward measured at 25° C. as constant temperature on a ship or on land.

The sampled marine water were hoisted up to be bought. And then, actual pH was afterward measured at 25° C. as constant temperature on a ship or on land. A glass pH electrode: PH2401C, which is available from RADIOMETER Corporation and is a tradename, was used for thus measurement. The data are shown in FIG. 14. As shown in FIG. 14, the converted pH data at 25° C. match up with the actual pH which were afterward measured at 25° C., approximately. Heretofore, there were no technical procedures for obtaining converted pH data at 25° C. from raw pH data measured at sea abyss in the ocean. However, according to the method of measuring pH of the analyte solution of the present invention, it is evident that pH of the analyte solution can be rigorously and accurately measured with extreme precision and there is scarcely difference against the actual pH. And it is shown that errors against the actual pH in Example 1 are extremely smaller than ones in Reference Example 1. It seems that the reason is to be enable to convert them into the accurate pH by the method of measuring pH of the analyte solution of the present invention.

As described above, according to the method of measuring pH by using the pH measuring device for the analyte solution of the present invention, pH of the analyte solution being measured can be simply, rigorously and accurately detected with extreme precision on site. It is unnecessary to afterward measure pH after sampling them.

Furthermore, as regards prior art, it has been trouble that calibration is usually preformed using 2 kinds of standard solutions for calibration points between which an expected pH value is included when measuring pH at 25° C. of room temperature. If one standard solution is used therefor, considerable measurement errors have been occurred after valuable calibration. Or more considerable measurement errors have been caused by variable pH change in the ocean on site. Therefore it has been difficult and troublesome to measure pH accurately.

However, the pH measuring device for the analyte solution of the present invention can measure pH accurately and simply, because pH values are calibrated from measured liquid temperature by using the predetermined equations.

INDUSTRIAL APPLICABILITY

The method of measuring pH of the analyte solution of the present invention is used for measuring pH of the analyte solution, especially pH of marine water, at sea abyss in the ocean on site by using available and stable pH standard solutions for the glass electrode or the reference electrode while utilizing temperature dependency.

EXPLANATIONS OF LETTERS OR NUMERALS

Numerals mean as follows. 1: pH measuring device for analyte solution, 10: glass electrode, 11: internal electrode, 12: glass electrode internal liquid, 13: pH sensing glass, 20: reference electrode, 21: internal electrode, 22: reference electrode internal liquid, 23: liquid junction, 30: voltage sensor, 40: temperature sensor, 50: analyte solution, 60: CPU, 71: passing water hole, 72: opened cover, 73: pressure resistance vessel.

What is claimed is:

1. A method of measuring pH of an analyte solution comprising:
    a step for sensing the liquid temperature of the analyte solution,
    a step for calculating a compensated pH value in the reference electrode internal liquid comprising:
        using electrodes, in which a pair of the electrodes consists of a glass electrode which encloses a glass electrode internal liquid including potassium chloride and a glass electrode buffer solution inside and a reference electrode which encloses a reference electrode internal liquid including potassium chloride and a reference electrode buffer solution inside,
        calculating a corrected pH value of the reference electrode buffer solution from an inherent pH value of the reference electrode buffer solution according to the liquid temperature,
        calculating a value of a potential variation of the reference electrode internal liquid according to the concentration of the potassium chloride thereof,
        calculating a deducted pH value of the reference electrode internal liquid from the value of the potential variation according to the liquid temperature, and then,
        compensating the deducted pH value of the reference electrode internal liquid from the corrected pH value of the reference electrode buffer solution,
    a step for sensing a voltage generated between the electrodes in the analyte solution, and
    a step for detecting a pH value of the analyte solution comprising:
        calculating a pH difference from the voltage according to the liquid temperature while compensating pH by a concentration of the potassium chloride in the reference electrode internal liquid and a liquid temperature of the analyte solution, and then
        detecting the pH value of the analyte solution from the pH difference according to the compensated pH value of the reference electrode internal liquid.

2. The method of measuring pH of the analyte solution according to claim 1, comprising:
    using the electrodes, in which a potential difference between the pair of the electrodes is regulated to 0 mV in a solution having out-of-range of pH 7.2 to 8.2.

3. The method of measuring pH of the analyte solution according to claim 1, further comprising a step for converting the pH value of the analyte solution into a predetermined value thereof at room temperature.

4. The method of measuring pH of the analyte solution according to claim 1, wherein the glass electrode internal liquid and the reference electrode internal liquid are equivalent each other.

5. The method of measuring pH of the analyte solution according to claim 1, wherein the glass electrode internal liquid and the reference electrode internal liquid are saturated with the potassium chloride respectively.

6. The method of measuring pH of the analyte solution according to claim 1, wherein the analyte solution is a salt-including sample solution or a plain water sample solution of selected from the group consisting of marine water, lake water and river water, or a sample solution contaminated with salts.

7. The method of measuring pH of the analyte solution according to claim 1, wherein the glass electrode has a glass sensing-membrane, and the reference electrode has a liquid junction.

8. The method of measuring pH of the analyte solution according to claim 2, wherein a difference between the corrected pH value of the reference electrode internal liquid and the pH value of the analyte solution is 2 at maximum.

9. A pH measuring device for an analyte solution comprising:
    electrodes which consist of a glass electrode that encloses a glass electrode internal liquid including potassium chloride and a glass electrode buffer solution inside and a reference electrode that encloses a reference electrode internal liquid including potassium chloride and a reference electrode buffer solution inside, a voltage sensor which senses a voltage generated between the electrodes in the analyte solution where the electrodes are dipped therein, a temperature sensor which senses a liquid temperature of the analyte solution, calculating circuits which calculate a corrected pH value of the reference electrode buffer solution from an inherent pH value of the reference electrode buffer solution according to the liquid temperature, calculate a value of a potential variation of the reference electrode internal liquid according to the concentration of the potassium chloride thereof, calculate a deducted pH value of the reference electrode internal liquid from the value of the potential variation according to the liquid temperature, and then, compensate the deducted pH value of the reference electrode internal liquid from the corrected pH value of the reference electrode buffer solution, calculate a compensated pH value in the reference electrode internal liquid, calculate a pH difference from the voltage according to the liquid temperature while compensating pH by a concentration of the potassium chloride in the reference electrode internal liquid and the liquid temperature of the analyte solution, and then calculate the pH value of the analyte solution from the pH difference according to the compensated pH value of the reference electrode internal liquid.

10. The pH measuring device for an analyte solution according to claim 9, wherein a potential difference between the electrodes is regulated to 0 mV in a solution having out-of-range of pH 7.2 to 8.2.

\* \* \* \* \*